(12) United States Patent
Kranzler et al.

(10) Patent No.: US 7,820,643 B2
(45) Date of Patent: *Oct. 26, 2010

(54) METHODS OF TREATING FIBROMYALGIA SYNDROME, CHRONIC FATIGUE SYNDROME AND PAIN

(75) Inventors: Jay D. Kranzler, La Jolla, CA (US); Srinivas G. Rao, San Diego, CA (US)

(73) Assignee: Cypress Bioscience, Inc., San Diego, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 10/623,431

(22) Filed: Jul. 18, 2003

(65) Prior Publication Data

US 2004/0019116 A1    Jan. 29, 2004

Related U.S. Application Data

(63) Continuation of application No. 10/028,547, filed on Dec. 19, 2001, now Pat. No. 6,602,911, which is a continuation-in-part of application No. 10/014,149, filed on Nov. 5, 2001, now Pat. No. 6,635,675.

(51) Int. Cl.
*A61K 31/33* (2006.01)
*A61K 9/00* (2006.01)
*A61K 31/165* (2006.01)
*A61K 31/16* (2006.01)
*A61K 31/50* (2006.01)
*A61K 31/415* (2006.01)

(52) U.S. Cl. ............. 514/183; 514/210.12; 514/252.01; 514/579; 514/617; 514/385

(58) Field of Classification Search ................. 514/620, 514/183

See application file for complete search history.

(56) References Cited

U.S. PATENT DOCUMENTS

| | | |
|---|---|---|
| 4,478,836 A | 10/1984 | Mouzin |
| 4,708,834 A | 11/1987 | Cohen |
| 4,710,384 A | 12/1987 | Rotman |
| 4,734,285 A | 3/1988 | Alderman |
| 4,740,198 A | 4/1988 | Theeuwes |
| 4,756,911 A | 7/1988 | Drost et al. |
| 4,761,501 A | 8/1988 | Husbands et al. |
| 4,775,535 A | 10/1988 | Lowey |
| 4,781,919 A | 11/1988 | Liebowitz |
| 4,784,858 A | 11/1988 | Ventouras |
| 4,792,448 A | 12/1988 | Ranade |
| 4,795,327 A | 1/1989 | Gaylord et al. |
| 4,795,642 A | 1/1989 | Cohen et al. |
| 4,795,645 A | 1/1989 | Friedman et al. |
| 4,798,725 A | 1/1989 | Patel |
| 4,800,083 A | 1/1989 | Hom et al. |
| 4,803,076 A | 2/1989 | Ranade |
| 4,803,079 A | 2/1989 | Hsiao et al. |
| 4,806,359 A | 2/1989 | Radebaugh et al. |
| 4,816,262 A | 3/1989 | McMullen |
| 4,820,522 A | 4/1989 | Radebaugh et al. |
| 4,822,619 A | 4/1989 | Eichel et al. |
| 4,824,678 A | 4/1989 | Lindahl et al. |
| 4,832,957 A | 5/1989 | Dempski et al. |
| 4,837,032 A | 6/1989 | Ortega |
| 4,839,177 A | 6/1989 | Colombo et al. |
| 4,842,866 A | 6/1989 | Horder et al. |
| 4,849,229 A | 7/1989 | Gaylord et al. |
| 4,861,590 A | 8/1989 | Grodberg |
| 4,863,743 A | 9/1989 | Hsiao et al. |
| 4,871,548 A | 10/1989 | Edgren et al. |
| 4,882,167 A | 11/1989 | Jang |
| 4,891,233 A | 1/1990 | Belanger et al. |
| 4,892,742 A | 1/1990 | Shah |
| 4,956,388 A | 9/1990 | Robertson et al. |
| 5,034,541 A | 7/1991 | Bigg |
| 5,397,574 A | 3/1995 | Chen |
| 5,399,359 A | 3/1995 | Baichwal |
| 5,399,362 A | 3/1995 | Baichwal et al. |
| 5,419,917 A | 5/1995 | Chen et al. |

(Continued)

FOREIGN PATENT DOCUMENTS

CA    2431041    7/2002

(Continued)

OTHER PUBLICATIONS

DRUGU AN 1992-39596, Moreau, G et al, Fundam.Clin.Pharmacol. 6 (4-5) 226, 1992, abstract.*

(Continued)

*Primary Examiner*—Ardin Marschel
*Assistant Examiner*—Alicia R Hughes
(74) *Attorney, Agent, or Firm*—Finnegan, Henderson, Farabow, Garrett & Dunner, LLP

(57) ABSTRACT

The present invention provides a method of treating fibromyalgia syndrome (FMS), chronic fatigue syndrome (CFS), and pain in an animal subject. The method generally involves administering a therapeutically effective amount of a dual serotonin norepinephrine reuptake inhibitor compound or a pharmaceutically acceptable salt thereof, wherein said dual serotonin norepinephrine reuptake inhibitor compound is characterized by a non-tricyclic structure and an equal or greater inhibition of norepinephrine reuptake than serotonin reuptake. In particular, the use of milnacipran to treat FMS, CFS, and pain is disclosed.

8 Claims, No Drawings

U.S. PATENT DOCUMENTS

| | | | |
|---|---|---|---|
| 5,422,123 A | 6/1995 | Conte et al. |
| 5,456,921 A | 10/1995 | Mateescu et al. |
| 5,458,005 A | 10/1995 | Perelshteyn |
| 5,458,887 A | 10/1995 | Chen et al. |
| 5,458,888 A | 10/1995 | Chen |
| 5,464,633 A | 11/1995 | Conte et al. |
| 5,472,708 A | 12/1995 | Chen |
| 5,512,297 A | 4/1996 | Baichwal |
| 5,532,244 A | 7/1996 | Wong et al. |
| 5,532,250 A | 7/1996 | Wong et al. |
| 5,532,268 A | 7/1996 | Wong et al. |
| 5,603,956 A | 2/1997 | Mateescu et al. |
| 5,621,142 A | 4/1997 | Mochizuki |
| 5,725,883 A | 3/1998 | Staniforth et al. |
| 5,744,474 A | 4/1998 | Thor |
| 5,773,025 A | 6/1998 | Baichwal |
| 5,776,969 A | 7/1998 | James |
| 5,792,796 A | 8/1998 | Woodruff et al. |
| 5,824,638 A | 10/1998 | Burnside et al. |
| 5,834,023 A | 11/1998 | Chen |
| 5,837,379 A | 11/1998 | Chen et al. |
| 5,885,616 A | 3/1999 | Hsiao et al. |
| 5,897,876 A | 4/1999 | Rudnic et al. |
| 5,912,013 A | 6/1999 | Rudnic et al. |
| 5,912,256 A | 6/1999 | Koch et al. |
| 5,916,595 A | 6/1999 | Chen et al. |
| 5,942,549 A | 8/1999 | Vargas |
| 5,945,416 A | 8/1999 | Shannon et al. |
| 5,952,004 A | 9/1999 | Rudnic et al. |
| 6,004,582 A | 12/1999 | Faour et al. |
| 6,028,070 A | 2/2000 | Heiligenstein |
| 6,066,643 A | 5/2000 | Perry |
| 6,077,541 A | 6/2000 | Chen et al. |
| 6,096,340 A | 8/2000 | Chen et al. |
| 6,099,859 A | 8/2000 | Cheng et al. |
| 6,099,862 A | 8/2000 | Chen et al. |
| 6,103,263 A | 8/2000 | Lee et al. |
| 6,106,862 A | 8/2000 | Chen et al. |
| 6,110,498 A | 8/2000 | Rudnic et al. |
| 6,184,222 B1 | 2/2001 | Heiligenstein |
| 6,380,200 B1 | 4/2002 | Mylari |
| 6,395,788 B1 | 5/2002 | Iglehart, III |
| 6,432,989 B1 * | 8/2002 | Chen | 514/348 |
| 6,441,038 B1 | 8/2002 | Loder et al. |
| 6,451,788 B1 | 9/2002 | Horrobin et al. |
| 6,489,341 B1 | 12/2002 | Jerussi |
| 6,500,853 B1 * | 12/2002 | Seehra et al. | 514/415 |
| 6,596,900 B2 | 7/2003 | Blakemore et al. |
| 6,602,911 B2 | 8/2003 | Kranzler et al. |
| 6,635,675 B2 | 10/2003 | Kranzler et al. |
| 6,964,962 B2 | 11/2005 | Wong et al. |
| 6,992,110 B2 | 1/2006 | Kranzler et al. |
| 7,005,452 B2 | 2/2006 | Deregnaucourt et al. |
| 2001/0036943 A1 | 11/2001 | Coe et al. |
| 2002/0006963 A1 | 1/2002 | Young et al. |
| 2002/0010216 A1 | 1/2002 | Rogosky et al. |
| 2002/0086864 A1 | 7/2002 | Wong et al. |
| 2002/0094986 A1 | 7/2002 | Chappell et al. |
| 2002/0147196 A1 | 10/2002 | Quessy et al. |
| 2002/0156067 A1 | 10/2002 | Wong et al. |
| 2002/0187958 A1 | 12/2002 | Horrobin et al. |
| 2003/0013689 A1 | 1/2003 | Helton et al. |
| 2003/0082214 A1 | 5/2003 | Williams et al. |
| 2003/0082225 A1 | 5/2003 | Mason |
| 2003/0130353 A1 | 7/2003 | Kranzler et al. |
| 2003/0143548 A1 | 7/2003 | Camilleri et al. |
| 2003/0203055 A1 | 10/2003 | Rao et al. |
| 2003/0232805 A1 | 12/2003 | Kranzler et al. |
| 2004/0014739 A1 | 1/2004 | Koppel |
| 2004/0019116 A1 | 1/2004 | Kranzler et al. |
| 2004/0034101 A1 | 2/2004 | Rao et al. |
| 2004/0063628 A1 * | 4/2004 | Piccariello et al. | 514/12 |
| 2004/0106681 A1 | 6/2004 | Rao et al. |
| 2004/0132826 A1 | 7/2004 | Hirsh et al. |
| 2004/0228830 A1 | 11/2004 | Hirsh et al. |
| 2004/0229956 A1 | 11/2004 | Kranzler et al. |
| 2005/0014843 A1 | 1/2005 | Allen et al. |
| 2005/0032782 A1 | 2/2005 | Rao et al. |
| 2005/0096395 A1 | 5/2005 | Rao et al. |
| 2006/0024366 A1 | 2/2006 | Hirsh et al. |
| 2007/0072946 A1 | 3/2007 | Rao et al. |
| 2007/0225375 A1 | 9/2007 | Kranzler et al. |
| 2008/0034101 A1 | 2/2008 | Tran et al. |
| 2008/0058317 A1 | 3/2008 | Rao et al. |
| 2008/0058318 A1 | 3/2008 | Rao et al. |
| 2008/0293820 A1 | 11/2008 | Rao et al. |

FOREIGN PATENT DOCUMENTS

| | | |
|---|---|---|
| EP | 0 814 084 | 12/1997 |
| EP | 0 818 198 | 1/1998 |
| EP | 0 759 299 B1 | 4/2000 |
| FR | 2 752 732 | 3/1998 |
| GB | 2 362 826 A | 12/2001 |
| WO | WO 94/00114 A1 | 1/1994 |
| WO | WO 95/22521 | 8/1995 |
| WO | 96/12485 | 5/1996 |
| WO | WO 97/10816 | 3/1997 |
| WO | WO 97/35574 | 10/1997 |
| WO | WO 97/35584 | 10/1997 |
| WO | WO 98/08495 | 3/1998 |
| WO | WO 98/36744 | 8/1998 |
| WO | 98/47491 | 10/1998 |
| WO | WO 99/15176 | 4/1999 |
| WO | WO 99/59593 | 11/1999 |
| WO | 00/10551 | 3/2000 |
| WO | 00/15223 | 3/2000 |
| WO | WO00/32178 * | 8/2000 |
| WO | 00/56310 | 9/2000 |
| WO | 00/56318 | 9/2000 |
| WO | 00/76956 | 12/2000 |
| WO | WO 01/26623 | 4/2001 |
| WO | 01/38293 | 5/2001 |
| WO | WO 00/32178 | 6/2002 |
| WO | WO 02/053140 A2 | 7/2002 |
| WO | WO 03/039598 A1 | 5/2003 |
| WO | WO 03/053426 | 7/2003 |
| WO | WO 03/068211 A1 | 8/2003 |
| WO | WO 2004/009069 | 1/2004 |
| WO | WO 2004/030633 | 4/2004 |
| WO | WO 2004/045718 A2 | 6/2004 |
| WO | WO 2007/038620 | 4/2007 |
| WO | WO 2008/019388 | 2/2008 |
| WO | WO 2008/021932 | 2/2008 |

OTHER PUBLICATIONS

DRUGU AN 1983-01770, Woerz zum Thema R, Muench.Med. Wochenschr. 124 (40) 855-56, 1982, abstract.*

EMBASE AN 1998129084, Prescrire International, 1998, 7/34, 51-53, abstract.*

EMBASE AN 90228858, Macher J et al, Neuropsychobiology, 1989, 22/2, 77-82, abstract.*

Medline AN 2001337451, Barkin et al, Am J Therapeutics, Jan. 2000, 7(1) 31-47, abstract.*

Medline AN 2001240387, Enggaard et al, Clin pharmacol therapeutics, Apr. 2001, 69(4) 245-51, abstract.*

Medline AN 97363915, Aronson, Clin therapeutics, May-Jun. 1997, 19(3) 420-32, abstract.*

Medline AN 97229930, Lewis et al, Am j health-system pharmacy, Mar. 15, 1997, 54(6) 643-52, abstract.*

Briley, M., "Milnacipran, A Double Noradrenaline and Serotonin Reuptake Inhibiting Antidepressant," European Neuropsychopharmacology, vol. 6, Supplement 4, p. S4 (Sep. 1996).*

Ardid, at al., "Antidepressants and pain," La Lettre de Pharmacologue 13: 8 (1993).

Cypress Bioscience, Inc., Investor Fact Sheet, Aug. 2001.

Dryson, "Venflaxine and fibromyalgia," NZ Med. J. 113(1105): 87 (2000).

Nagaoka, et al., "Beneficial effects of a serotonin-noradrenaline reuptake inhibitor on fibromyalgia syndrome: a case report," Med. Drug. J. 37: 10 (2001).

Noguchi, at al., "Open channel block of NMDA receptors by conformationally restricted analogs of milnacipran and their protective effect against NMDA-induced neurotoxicity," Synapse 31: 87-96 (1999).

Shuto, et al., "(±)-Z-2-(Aminomethyl)-1-phenylcyclopropanecarboximide derivatives as a new prototype of NMDA receptor antagonists," J. Med. Chem. 38: 2964-2968 (1995).

Shuto, et al., "(1S,2R)-1-(phenyl-2-[(s)-1-aminopropyl]-N,N-diethylcyclopropanecarboxamide (PPDC), a new class of NMDA-receptor antagonist: molecular design by a novel conformational restriction strategy," Jpn. J. Pharmacol. 85: 207-213 (2001).

Shuto, at al., "Synthesis and biological activity of conformationally restricted analogs of milnacipran: (lS,2R)-1-(phenyl-2-[(S)-1aminopropyl]-N,N-diethylcyclopropenecarboxamide, an efficient noncompetitive N-methyl-D-aspartic acid receptor antagonist," J. Med. Chem. 39: 4844-4852 (1996).

Shuto, et al., "Synthesis and biological activity of conformationally restricted analogues of milnacipran: (1S,2R)-1-phenyl-2-[(r)-1-amino-2-propynyl]-N,N-diethylcyclopropane-carboximide is a novel class of NMDA receptor channel blocker," J. Med. Chem. 41: 3507-3514 (1998).

Rao et al., The neuropharmacology of centrally-acting analgesic medications in fibromyalgia, Theum. Dis. Clin. N. Am. 28 (2002) 235-259.

Ninan, M.D., Philip T., Use of Venlafaxine in Other Psychiatric Disorders, Depression and Anxiety 12(1) (2000) 90-94.

Nutt et al., Potential Applications of Venlafaxine, Rev. Contemp. Pharmacother. 9 (1998) 321-331.

Dwight et al., An Open Clinical Trial of Venlafaxine Treatment of Fibromyalgia, Psychsomatics 39(1) (1998) 14-17.

Goodnick et al., Psychotropic Treatment of Chronic Fatigue Syndrome and Related Disorders, J. Clin. Psychiatry 54(1) (1993) 13-20.

Fuller, Clinical Applications of 5-HT Uptake Inhibitors, Advances in the Biosciences, vol. 85, pp. 255-270, 1992.

Lecrubier, Milnacipran: The Clinical Properties of a Selective Serotonin and Noradrenaline Reuptake Inhibitor (SNRI), Human Psychopharmacol. Clin., vol. 12, pp. S127-S134, 1997.

Farthing, New Drugs in the Management of the Irritable Bowel Syndrome, Drugs, vol. 56, pp. 11-21, 1998.

O'Malley, et al., Treatment of Fibromyalgia with Antidepressants, J. Gen. Intern. Med., vol. 15, pp. 659-666, 2000.

Mertz, Irritable Bowel Syndrome, N. Engl. J. Med., vol. 349(22), pp. 2136-2146, 2003.

Fennerty, Traditional Therapies for Irritable Bowel Syndrome: An Evidence-Based Appraisal, Rev. Gastroenterol. Disord., vol. 3, Suppl. 2, pp. 18-24, 2003.

Patel, et al., The Placebo Effect in Irritable Bowel Syndrome Trials: A Meta-Analysis, Neurogastroenterol. Motil., vol. 17, , pp. 332-340, 2005.

Chart of Cypress Bioscience applications related to milnacipran for treatment of various disorders.

Aaron et al., "Overlapping conditions among patients with chronic fatigue syndrome, fibromyalgia, and temporomandibular disorder," Arch. Intern. Med., 160: 221-227 (2000).

Alagiri et al., "Interstitial cystitis: unexplained associations with other chronic disease and pain syndromes," Urology, 49(Suppl. 5A): 52-57 (1997).

Anderberg et al., "Citalopram in patients with fibromyalgia—a randomized, double-blind, placebo-controlled study," Eur. J. Pain, 4: 27-35 (2000).

Ansari, "The efficacy of newer antidepressants in the treatment of chronic pain: a review of current literature," Harv. Rev. Psychiatry, 7: 257-277 (2000).

Atkinson et al., "Effects of noradrenergic and serotonergic antidepressants on chronic low back pain intensity," Pain, 83: 137-145 (1999).

Barkin, "The management challenges of chronic pain: the roll of antidepressants," Am. J. Ther., 7: 31-47 (2000).

Bennett, "Pharmacological treatment of fibromyalgia," J. Functional Syndromes, 1: 79-92 (2001).

Buskila, "Drug therapy," Baillieres Best Pract. Res. Clin. Rheumatol., 13: 479-485 (1999).

Caccia, "Metabolism of the newer antidepressants: an overview of the pharmacological and pharmacokinetic implications," Clin. Pharmacokinet., 34: 281-302 (1998).

Carette et al., "Comparison of amitriptyline, cyclobenzaprine, and placebo in the treatment of fibromyalgia. A randomized, double-blind clinical trial," Arthritis Rheum., 37: 32-40 (1994).

Clauw, "The pathogenesis of chronic pain and fatigue syndromes, with special reference to fibromyalgia," Med. Hypotheses, 44: 369-378 (1995).

Clauw et al., "Chronic Pain and Fatigue Syndromes: Overlapping Clinical and Neuroendocrind Features and Potential Pathogenic Mechanisms," Neuroimmunomodulation, 4:134-153 (1997).

Dworkin et al., "Clinical aspects of depression in chronic pain patients," Clin. J. Pain, 7: 79-94 (1991).

Eisen, "Venlafaxine therapy for vulvodynia," The Pain Clinic, 8: 365-367 (1995).

Farthing, "Irritable bowel syndrome: new pharmaceutical approaches to treatment," Bailllieres Best Pract. Res. Clin. Gastroenterol., 13: 461-471 (1999).

Fishbain, "Evidence-based data on pain relief with antidepressants," Ann. Med., 32: 305-316 (2000).

Giamberardino, "Recent and forgotten aspects of visceral pain," Eur. J. Pain, 3: 7-92 (1999).

Goldenberg et al., "A randomized, controlled trial of amitriptyline and naproxen in the treatment of patients with fibromyalgia," Arthritis Rheum., 29: 1371-1377 (1986).

Goldenberg et al., "A randomized, double-blind crossover trial of fluoxetine and amitriptyline in the treatment of fibromyalgia," Arthritis Rheum., 39: 1852-1859 (1996).

Gruber et al., "The management of treatment-resistant depression in disorders on the interface of psychiatry and medicine," The Psychiatric Clinics of North America, 19: 351-369 (1996).

Hannonen et al., "A randomized, double-blind, placebo-controlled study of miclobemide and amitriptyline in the treatment of fibromyalgia in females without psychiatric disorder," Br. J. Rheumatol., 37: 1279-1286 (1998).

Jain, "Addressing both the emotional and physical symptoms in depression," Medscape CME program (2003).

Jung et al., "The efficacy of selective Serotonin reuptake inhibitors for the management of chronic pain," J. Gen. Intern. Med., 12: 384-389 (1997).

Kent, "SNaris, NaSSAs, and NaRls: new agents for the treatment of depression," Lancet, 355: 911-918 (2000).

Kranzler et al., "The psychopharmacology of fibromyalgia: a drug development perspective", Psychopharmacol Bull., 36: 165-213 (2002).

Lautenschlager, "Present state of medication therapy in fibromyalgia syndrome," Scand. J. Rheumatol. Suppl., 113: 32-36 (2000).

Leventhal, "Management of fibromyalgia," Ann. Intern. Med., 131: 850-858 (1999).

Martindale, Antidepressants, Pharmaceutical Press, London, $32^{nd}$ ed., pp. 271, 284, 298, 1485 (1999).

Max et al., "Effects of desipramine, amitriptyline, and fluoxetine on pain diabetic neuropathy," N. Engl. J. Med., 326: 1250-1256 (1992).

Montgomery, "Venlafaxine: a new dimension in antidepressant pharmacotherapy," J. Clin. Psychiatry, 54: 119-126 (1993).

Nicolodi et al., "Fibromyalgia and headache. Failure of serotonergic analgesia and N-methyl-d-aspartate-mediated neuronal plasticity: their common clues," Cephalalgia, Supp.21: 41-44 (1998).

Norregaard et al., "A randomized controlled trial of citalopram in the treatment of fibromyalgia," Pain, 61: 445-449 (1995).

Novick et al., "A randomized, double-blind, placebo-controlled trial of tegaserod in female patients suffering from irritable bowel syndrome with constipation," *Aliment Pharmacol. Ther.*, 16: 1877-1888 (2002).

Pande et al., "Three randomised, placebo-controlled, double-blind trials of pregabalin treatment of generalized anxiety disorder (GAD)," 10(Suppl. 3): 344 Abstract (2000).

Peghini et al., "Imipramine decreases oesophageal pain perception in human male volunteers," *Gut*, 42: 807-813 (1998).

Puech et al., "Milnacipran, a new serotonin and noradrenaline reuptake inhibitor: an overview of its antidepressant activity and clinical tolerability," *Int. J. Psychopharm.*, 12: 99-108 (1997).

Quijada-Carrera et al., "Comparison of tenoxicam and bromazepan in the treatment of fibromyalgia: a randomized, double-blind, placebo-controlled trial," *Pain*, 65: 221-225 (1996).

Rao et al., "Pharmacological therapies in fibromyalgia," *Best Prod. Res. Clin. Rheumatol.*, 17: 611-627 (2003).

Reneric et al., "Antidepressant behavioral effects by dual inhibition of monoamine reuptake in the rat forced swimming test," *Psychopharmacology*, 136: 190-197 (1998).

Ruoff, "Depression in the patient with chronic pain," *The Journal of Family Practice*, 43: S25-S33 (1996).

Saper et al., "Nefazodone for chronic daily headache prophylaxis: an open-label study," *Headache*, 41: 465-474 (2001).

Shuto et al., "Synthesis of (+) and (−) milnaciprans and their conformationally restricted analogs," *Tetrahedron Lett.*, 37: 641-644 (1996).

Sindrup et al., "Efficacy of pharmacological treatment of neuropathic pain: an update and effect related to mechanism of drug action," *Pain*, 83: 389-400 (1999).

Swaynok et al., "Peripheral antinociceptive actions of desipramine and fluoxetine in an inflammatory and neuropathic pain test in the rat," *Pain*, 82: 149-158 (1999).

Thema, "The drug induced alleviation of carcinoma pain," *Much. Med. Wochenschr*, 124:855-856 (1982).

Vaishnavi et al., "Milnacipran: A comparative analysis of human monoamine uptake and transporter binding affinity," *Biol Psychiatry*, 55: 320-322 (2004).

Vitton et al., "A double-blind placebo-controlled trial of milnacipran in the treatment of fibromyalgia," *Hum Psychopharmacol Clin Exp*, 19: S27-S35 (2004).

Watson et al., "Amitriptyline versus maprotiline in postherpetic neuralgia: a randomized, double-blind, crossover trial," *Pain*, 48: 29-36 (1992).

Wesselman, "Interstitial cystitis: A chronic visceral pain syndrome," *Urology*, 57(Suppl. 64): 32-39 (2001).

Wessely et al., "Functional somatic syndromes: one or many?," *Lancet*; 354: 936-939 (1999).

Wolfe et al., "A double-blind placebo controlled trial of fluoxetine in fibromyalgia," *Scand. J. Rheum.*, 23: 255-259 (1994).

Woolf et al., "Neuropathic pain: aetiology, symptoms, mechanisms, and management," *Lancet*, 353: 959-1964 (1999).

Yunus et al., "Towards a model of pathophysiology of fibromyalgia: aberrant central pain mechanisms with peripheral modulation," *J. Rheumatol.*, 19: 846-850 (1992).

Restriction Requirement dated Oct. 20, 2006, in U.S. Appl. No. 10/678,767, filed Oct. 3, 2003.

Response to Restriction Requirement dated Nov. 16, 2006, in U.S. Appl. No. 10/678,767, filed Oct. 3, 2003.

Office Action dated Feb. 20, 2007, in U.S. Appl. No. 10/678,767, filed Oct. 3, 2003.

Response to Office Action Under 37 C.F.R. 1.111 dated Jun. 7, 2007, in U.S. Appl. No. 10/678,767, filed Oct. 3, 2003.

Office Action dated Aug. 27, 2007, in U.S. Appl. No. 10/678,767, filed Oct. 3, 2003.

Response to Office Action Under 37 C.F.R. 1.111 dated Nov. 27, 2007, in U.S. Appl. No. 10/678,767, filed Oct. 3, 2003.

Final Office Action dated Feb. 25, 2008, in U.S. Appl. No. 10/678,767, filed Oct. 3, 2003.

Response to Final Office Action Under 37 C.F.R. 1.116 dated Apr. 15, 2008, in U.S. Appl. No. 10/678,767, filed Oct. 3, 2003.

Advisory Action dated May 12, 2008, in U.S. Appl. No. 10/678,767, filed Oct. 3, 2003.

Office Action dated Aug. 22, 2008, in U.S. Appl. No. 10/678,767, filed Oct. 3, 2003.

Response to Office Action Under 37 C.F.R. 1.111 dated Nov. 24, 2008, in U.S. Application No. 10/678,767, filed Oct. 3, 2003.

Final Office Action dated Mar. 4, 2009, in U.S. Appl. No. 10/678,767, filed Oct. 3, 2003.

Office Action dated Sep. 27, 2007, in U.S. Appl. No. 11/752,213, filed May 22, 2007.

Response to Office Action dated Dec. 27, 2007, in U.S. Appl. No. 11/752,213, filed May 22, 2007.

Interview Summary dated Jan. 10, 2008, in U.S. Application No. 11/752,213, filed May 22, 2007.

Restriction Requirement dated Feb. 4, 2008, in U.S. Appl. No. 11/752,213, filed May 22, 2007.

Response to Restriction Requirement dated Mar. 4, 2008, in U.S. Application No. 11/752,213, filed May 22, 2007.

Office Action dated Aug. 12, 2008, in U.S. Appl. No. 11/752,213, filed May 22, 2007.

Response to Office Action dated Dec. 12, 2008, in U.S. Appl. No. 11/752,213, filed May 22, 2007.

Final Office Action dated Apr. 17, 2009, in U.S. Appl. No. 11/752,213, filed May 22, 2007.

Applicant Statement of Interview Summary dated May 7, 2009, in U.S. Appl. No. 11/752,213, filed May 22, 2007.

Amendment and Response to Office Action dated Jun. 17, 2009, in U.S. Appl. No. 11/752,213, filed May 22, 2007.

Office Action dated Sep. 18, 2008, in U.S. Patent Appl. No. 11/835,590, filed Aug. 8, 2007.

Amendment and Response dated Mar. 18, 2009, in U.S. Appl. No. 11/835,590, filed Aug. 8, 2007.

Final Office Action dated Jun. 4, 2009, n. U.S. Appl. No. 11/835,590, filed Aug. 8, 2007.

Office Action dated Oct. 7, 2008, in U.S. Appl. No. 11/835,620, filed Aug. 8, 2007.

Amendment and Response filed Apr. 6, 2009, in U.S. Appl. No. 11/835,620, filed Aug. 8, 2007.

Office Action dated Sep. 22, 2008, in U.S. Appl. No. 12/035,820, filed Feb. 22, 2008.

Amendment and Response to Office Action dated Oct. 21, 2008, in U.S. Appl. No. 12/035,820, filed Feb. 22, 2008.

Restriction Requirement dated Feb. 4, 2009, in U.S. Appl. No. 12/035,820, filed Feb. 22, 2008.

Amendment and Response to Restriction Requirement and Applicant Statement of Interview Summary dated Jun. 17, 2009, in U.S. Appl. No. 12/035,820, filed Feb. 22, 2008.

First Examination Report for Indian Application No. 496/DELNP/2005, dated Jun. 15, 2006.

Communication pursuant to Article 96(2) EPC dated Oct. 25, 2006, in European Application No. 03748971.3.

PCT International Preliminary Examination Report dated Feb. 5, 2004, in International Application No. PCT/US02/35396.

Amendment dated May 7, 2004, in European Application No. 02793880.2.

Communication pursuant to Article 96(2) EPC dated Jun. 1, 2005, in European Application No. 02793880.2.

Response with amended claims dated Nov. 24, 2005, in European Application No. 02793880.2.

Communication pursuant to Article 94(3) EPC dated Dec. 17, 2007, in European Application No. 02793880.2.

Response with amended claims dated Jun. 17, 2008, in European Application No. 02793880.2.

Examiner's first report dated Mar. 5, 2008 in Australian Application No. 2003284005.

Aaron et al., "A review of the evidence for overlap among unexplained clinical conditions", Ann. Intern. Med., vol. 134, No. 9.2, (2001), pp. 868-881.

Boissevain et al., "Toward an integrated understanding of fibromyalgia syndrome. I. Medical and pathophysiological aspects", Pain, vol. 45, No. 3, (1991), pp. 227-238.

Briley, "New hope in the treatment of painful symptoms in depression," Curr. Opin. Invest. Drugs, vol. 4, No. 1, (2003), pp. 42-45. Abstract.

Gendreau et al., "Efficacy of Milnacipran in Patients with Fibromyalgia," The Journal of Rheumatology, vol. 32, No. 10 (2005), pp. 1975-1984.
Kasper et al., "A placebo-controlled study of pregabalin and venlafaxine treatment of GAD", European neuropsychopharmacology, vol. 12, Suppl. 3, (Oct. 2002), pp. S341-S342.
Medline EMBASE 1998129084 1998 Milnacipran: New Preparation.
Moret et al., "Sensitivity of the response of 5-HT autoreceptors to drugs modifying synaptic availability of 5-HT", Neuropharmacology, vol. 27, No. 1, (1988), pp. 43-49.
Witter et al., "Chronic pain and fibromyalgia: the regulatory perspective", Best Practice Res Clin Rheumatology, vol. 17, No. 4, (2003), pp. 541-546.
Wolfe et al., "A double-blind Placebo Controlled Trial of Fluoxetine in Fibromyalgia", Scand. J. Rheum., vol. 23, No. 5, (1994), pp. 255-259.
Wolfe et al., "Health Status and Disease Severity in Fibromyalgia: Results of a Six-Center Longitudinal Study", Arthritis Rheum., vol. 40, No. 9, (1997), pp. 1571-1579.
Wolfe et al., "Preference of Nonsteroidal Antiinflammatory Drugs Over Acetaminophen by Rheumatic Disease Patients", Arthritis Rheumatism, vol. 43, No. 2, (2000), pp. 378-385.
Wolfe et al., "The American College of Rheumatology 1990 Criteria for the Classification of Fibromyalgia", Arthritis Rheumatism, vol. 33, No. 2 (1990) pp. 160-172.
Wolfe et al., "The Prevalence and Characteristics of Fibromyalgia in General Population", Arthritis Rheumatism, vol. 38, No. 1 (1995) pp. 19-28.
Yoshimura et al., "The involvement of the tetrodotoxin-resistant sodium channel Nav1.8 (PN3/SNS) in a rat model of visceral pain", J. Neurosci., vol. 21, No. 21, (2001), pp. 8690-8696.
PCT/US02/40976 (WO 03/053426), International Search Report dated May 2, 2003.
PCT/US02/40976 (WO 03/053426), International Preliminary Report on Patentability/Written Opinion dated Nov. 15, 2003.
PCT/US03/23088 (WO 2004/009069), International Search Report dated Dec. 11, 2003.
PCT/US03/23088 (WO 2004/009069), International Preliminary Report on Patentability/Written Opinion dated May 3, 2005.
PCT/US03/031622 (WO 2004/030633), International Search Report dated Jun. 3, 2004.
PCT/US03/031622 (WO 2004/030633), International Preliminary Report on Patentability/Written Opinion dated Jun. 3, 2004.
PCT/US2006/037714 (WO 2007/038620), International Search Report dated Aug. 23, 2007.
PCT/US2006/037714 (WO 2007/038620), International Preliminary Report on Patentability/Written Opinion dated Apr. 1, 2008.
PCT/US2007/075555 (WO 2008/019388), International Search Report dated Sep. 12, 2008.
PCT/US2007/075555 (WO 2008/019388), International Preliminary Report on Patentability/Written Opinion dated Feb. 10, 2009.
PCT/US2007/075549 (WO 2008/021932), International Search Report dated Sep. 19, 2008.
PCT/US2007/075549 (WO 2008/021932), International Preliminary Report on Patentability/Written Opinion dated Feb. 10, 2009.
PCT/US2008/064471 (WO 2008/147843), International Search Report dated Aug. 21, 2008.
PCT/US2008/064471 (WO 2008/147843), International Preliminary Report on Patentability/Written Opinion dated Nov. 24, 2009.
U.S. Appl. No. 10/678,767, filed Oct. 3, 2003, by Srinivas G. Rao et al.; Amendment accompanying request for continued examination dated Sep. 3, 2009.
U.S. Appl. No. 10/678,767, filed Oct. 3, 2003, by Srinivas G. Rao et al.; Non-Final Office Action dated Jan. 8, 2010.
U.S. Appl. No. 11/535,237, filed Sep. 26, 2006, by Srinivas G. Rao et al.; Non-Final Office Action dated Mar. 3, 2010.
U.S. Appl. No. 11/535,237, filed Sep. 26, 2006, by Srinivas G. Rao et al.; Restriction Requirement dated Oct. 23, 2009.
U.S. Appl. No. 11/752,213, filed May 22, 2007, by Jay D. Kranzler et al.; Non-Final Office Action dated Jun. 25, 2009.
U.S. Appl. No. 11/835,620, filed Aug. 8, 2007, by Srinivas G. Rao et al.; Final Office Action dated Jul. 2, 2009.
U.S. Appl. No. 12/035,820, filed Feb. 22, 2008, by Jay D. Kranzler et al.; Final Office Action dated Nov. 27, 2009.
U.S. Appl. No. 12/125,302, filed May 22, 2008, by Srinivas G. Rao et al.; Non-Final Office Action dated Nov. 23, 2009.
Reimann, et al., Effects of the Central Analgesic Tramadol on the Uptake and Release of Noradrenaline and dopamine in vitro, Br J Pharmacol. Mar. 1993; 108(3):806-11.
Reimann et al., Interaction of the Central Analgesic, Tramadol, with the Uptake and Release of 5-hydroxytryptamine in the rat brain in vitro, Br J Pharmacol. Jan. 1992; 105(1):147-51.
Hara, et al., The Effects of Tramadol and Its Metabolite on Glycine, -Aminobutyric AcidA, and N-Methyl-D-Aspartate Receptors Expressed in Xenopus Oocytes.
Bymaster et al., Comparative Affinity of Duloxetine and Venlafaxine for Serotonin and Norepinephrine Transporters in vitro and in vivo, Human Serotonin Receptor Subtypes, and Other Neuronal Receptors.
Reid et al., 2000, British Medical Journal 320:292-296.
Moret et al., 1985, Neuropharmacology 24 (12):1211-1219.
Palmer et al., 1989, Eur J Clin Pharmacol 37:235-238.
Sanchez et al., 1999, Cellular and Molecular Neurobiology 19(4):467-489.
Turcotte et al., 2001, Neuropsychopharmacolgy 24(5):511-521.
Moret et al., 1997, J. Neurochem. 69(2):815-822.
Bel et al., 1999, Neropsychopharmacology 21 (6):745-754.
Tatsumi et al., 1997, European Journal of Pharmacology 340:249-258.
Spencer and Wild, 1998, supra.
Viazzo et al., 1996, Tetrahedron Lett. 37(26):4519-4522.
Zelter et al., 2000, Pain 89:19-24.
Bennett et al., 1988 Pain 33:87-107.
Seltzer et al., 1990, Pain 43:205-218.
Kim et al., 1992, Pain 50:355-363.
Decosterd et al., 2000, Pain 87:149-158.
Jasmin et al., 1998, Pain 75:367-382.
Quintero et al., 2000, Pharmacology, Biochemistry and Behavior 67:449-458.
Doyle & Hu, "A new enantioselective synthesis of milnacipran and an analogue by catalytic asymmetirc cyclopropanation," Adv. Synth. Catal. 343(3):299-302 (2001).
Deprez, et al., "Which bioequivalence study for a racemic drug? Application to milnacipran," Eur. J. Drug Metab. Pharmacokinet. 23(2): 166-171(1998).

* cited by examiner

METHODS OF TREATING FIBROMYALGIA SYNDROME, CHRONIC FATIGUE SYNDROME AND PAIN

This application is a continuation of U.S. Ser. No. 10/028,547 filed on Dec. 19, 2001 which is a continuation-in-part of U.S. Ser. No. 10/014,149 filed on Nov. 5, 2001.

1. FIELD OF THE INVENTION

The present invention relates to methods for the treatment of fibromyalgia syndrome, chronic fatigue syndrome, and pain. In particular, the present invention relates to methods of treating fibromyalgia syndrome, chronic fatigue syndrome, and pain with a sub-class of dual serotonin norepinephrine reuptake inhibitors characterized by a non-tricyclic structure and inhibit the reuptake of norepinephrine to an equal or greater extent than they inhibit the reuptake of serotonin.

2. BACKGROUND OF THE INVENTION

Fibromyalgia syndrome (FMS) is the most frequent cause of chronic, widespread pain, estimated to affect 2-4% of the population. FMS is characterized by a generalized heightened perception of sensory stimuli. Patients with FMS display abnormalities in pain perception in the form of both allodynia (pain with innocuous stimulation) and hyperalgesia (increased sensitivity to painful stimuli). The syndrome, as defined by the American College of Rheumatology's criteria, involves the presence of pain for over 3 months duration in all four quadrants of the body, as well as along the spine. In addition, pain is elicited at 11 out of 18 "tender points" upon palpation. Other associated symptoms include fatigue, non-restorative sleep, and memory difficulties.

Chronic fatigue syndrome (CFS) is a debilitating disorder characterized by profound tiredness or fatigue. Patients with CFS may become exhausted with only light physical exertion, and must often function at a level of activity substantially lower than their capacity before the onset of illness. In addition to the key defining characteristic of fatigue, CFS patients generally report various nonspecific symptoms, including weakness, muscle aches and pains, excessive sleep, malaise, fever, sore throat, tender lymph nodes, impaired memory and/or mental concentration, insomnia, and depression. Like patients with FMS, patients with CFS suffer from disordered sleep, localized tenderness, and complaints of diffuse pain and fatigue.

There are two widely used criteria for diagnosing CFS. The criteria established by the U.S. Centers for Disease Control and Prevention include medically unexplained fatigue of at least six months duration that is of new onset, not a result of ongoing exertion and not substantially alleviated by rest, and a substantial reduction in previous levels of activity. In addition, the diagnosis involves the determination of the presence of four or more of the following symptoms—subjective memory impairment, tender lymph nodes, muscle pain, joint pain, headache, unrefreshing sleep, and postexertional malaise (>24 hours). Reid et al., 2000, *British Medical Journal* 320: 292-296. The diagnostic criteria from Oxford includes severe, disabling fatigue of at least six months duration that affects both physical and mental functioning and the fatigue being present for more than 50% of the time. In addition, the diagnosis involves the determination of the presence of other symptoms, particularly myalgia and sleep and mood disturbance. Reid et al., 2000, *British Medical Journal* 320: 292-296.

Owing to their common symptomology, FMS and CFS are thought to be related. However, they manifest different major symptoms. Whereas pain is the major symptom reported by patients with FMS, fatigue is the major symptom reported by patients with CFS. Given their relatedness, these two indications have been treated with the same medications. Some of the common medications currently employed to treat CFS and/or FMS include, but are not limited to, analgesics, hypnotics, immune suppressants, various other prescribed medications, and an array of non-prescription medications. Although a broad array of medications are used in FMS and CFS patients, no single pharmacological agent or combination of agents is effective in the treatment of either of these disorders. Thus, due to the lack of effective treatment regimens for FMS and/or CFS, there is a need to develop effective treatments.

Pain is associated with a variety of different underlying illnesses or injuries. Pain may be either acute or chronic. Chronic or intractable pain is often endured over many years or decades. Patients suffering from chronic pain often develop emotional problems which can lead to depression and in the worst case, attempted suicide. Long lasting pain often occurs particularly in joints, in muscles, connective tissue and in the back. In the United States alone, chronic pain causes a loss of more than 250 million working days per year. A patient is considered to have chronic pain when complaints thereof last longer than six months. In the course of time, chronic pain may form an independent clinical syndrome.

Most analgesic agents in use today are not always effective, may produce serious side effects and can be addictive. Hence, there is a demand for more active analgesic agents with diminished side effects and toxicity, and which are non-addictive. The ideal analgesic would reduce the awareness of pain, produce analgesia over a wide range of pain types, act satisfactorily whether given orally or parenterally, produce minimal or no side effects, and be free from the tendency to produce tolerance and drug dependence.

3. SUMMARY OF THE INVENTION

In one aspect, the invention provides a method of treating fibromyalgia syndrome (FMS) and/or the symptoms associated therewith in an animal subject, including a human. The method generally involves administering to an animal subject suffering from FMS an effective amount of a dual serotonin norepinephrine reuptake inhibitor ("SNRI") compound of a specific type, or a pharmaceutically acceptable salt thereof. The SNRI compounds that are useful to treat FMS and/or symptoms associated therewith are characterized by a non-tricyclic structure and inhibit the reuptake of norepinephrine to an equal or greater extent than they inhibit the reuptake of serotonin (referred to hereinafter as "NE≧5-HT SNRI compounds"). In one embodiment of the invention, the NE≧5-HT SNRI compound administered inhibits norepinephrine reuptake to a greater degree than it inhibits serotonin reuptake (referred to hereinafter as a "NE>5-HT SNRI compound"). One particular example of such a NE>5-HT SNRI compound is milnacipran, or a pharmaceutically acceptable salt thereof. In another embodiment, the NE≧5-HT SNRI compound is not administered adjunctively with phenylalanine, tyrosine and/or tryptophan.

In another aspect, the invention provides a method of treating pain in an animal subject, including a human. The method generally involves administering to an animal subject suffering from pain an effective amount of a NE≧5-HT SNRI compound, or a pharmaceutically acceptable salt thereof. In one embodiment, a NE≧5-HT SNRI compound is administered. One particular example of a NE>5-HT SNRI compound is milnacipran or a pharmaceutically acceptable salt thereof. In another embodiment, the NE≧5-HT SNRI compound is not administered adjunctively with phenylalanine, tyrosine and/or tryptophan.

In still another aspect, the invention provides a method of treating CFS and/or symptoms associated therewith. The method generally involves administering to a patient suffering from CFS an effective amount of a NE≧5-HT SNRI compound, or a pharmaceutically acceptable salt thereof. In one embodiment, a NE>5-HT SNRI compound is administered. One particular example of a NE>5-HT SNRI compound is milnacipran or a pharmaceutically acceptable salt thereof. In another embodiment, the NE≧5-HT SNRI compound is not administered adjunctively with phenylalanine, tyrosine and/or tryptophan.

In yet another aspect, the invention provides a kit comprising a NE≧5-HT SNRI compound packaged in association with instructions teaching a method of using the compound according to one or more of the above-described methods. The kit can contain the NE≧5-HT SNRI compound packaged in unit dosage form. In one embodiment, a NE>5-HT compound can be included in the kit. One particular example of a NE>5-HT SNRI compound is milnacipran or a pharmaceutically acceptable salt thereof.

4. DETAILED DESCRIPTION OF THE PREFERRED EMBODIMENTS

4.1 Abbreviations

| | |
|---|---|
| CFS | chronic fatigue syndrome |
| FMS | fibromyalgia syndrome |
| 5-HT | serotonin |
| NARIs | norepinephrine specific reuptake inhibitors |
| NE | norepinephrine |
| NMDA | N-methyl D-aspartate |
| NSAIDs | non-steroidal anti-inflammatory drugs |
| SSRIs | selective serotonin reuptake inhibitors |
| TCAs | tricyclic antidepressants |
| SNRIs | dual serotonin norepinephrine reuptake inhibitors |

4.2 Definitions

The term "dual serotonin norepinephrine reuptake inhibitor compound" or SNRI refers to the well-recognized class of anti-depressant compounds that selectively inhibit reuptake of both serotonin and norepinephrine. Common SNRI compounds include, but are not limited to, venlafaxine, duloxetine, and milnacipran.

The terms "NE≧5-HT SNRI" and "NE>5-HT SNRI" refer to particular subclasses of SNRI compounds that are useful in the methods and kits of the present invention, as will be described in more detail herein.

4.3 Treatment of FMS, CFS and/or Pain

The present invention provides methods and kits for treating FMS, CFS, and pain. A particular subclass of SNRI compounds is useful for practicing the present invention. Compounds in this SNRI subclass, referred to as "NE≧5-HT SNRI compounds," inhibit norepinephrine reuptake more than or equal to serotonin reuptake. Moreover, the NE≧5-HT compounds of the invention exclude compounds that belong to the distinct class of antidepressant compounds commonly referred to in the art as tricyclic antidepressants or TCAs. In particular, compounds useful for practicing the present invention inhibit norepinephrine reuptake more than serotonin reuptake, referred to as "NE>5-HT SNRI compounds."

Tricyclic antidepressants (TCAs) are a well-recognized class of antidepressant compounds that are characterized by a dibenz[b,e]azepine (structure I), dibenz[b,e]oxepine (structure II), dibenz[a,d]cycloheptane (structure III) or dibenz[a,d]cycloheptene (structure IV) tricyclic ring structure. These various rings are depicted below:

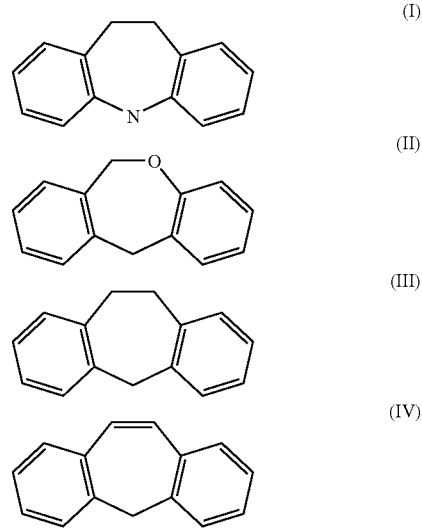

The TCAs are typically substituted at position 1 of the tricyclic ring with alkylamines or alkylidenamines, and may include additional substituents (typically on the benzo groups). Many common TCAs, including imipramine, desipramine, clomipramine, trimipramine, amitriptyline, nortriptyline, doxepin, cyclobenzaprine and protriptyline are characterized by the general formula (V), below:

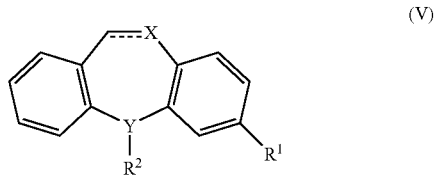

wherein:
X is O or C;
Y is N or C;
$R^1$ is H or Cl;
$R^2$ is selected from the group consisting of —$(CH_2)_3$N$(CH_3)_2$, —$(CH_2)_3$NHCH$_3$, —$CH_2$CH$(CH_3)$CH$_2$N$(CH_3)_2$, =CH$(CH_2)$N$(CH_3)_2$, =CH$(CH_2)_2$NHCH$_3$ and —$(CH_2)_3$NHCH$_3$; and
the dotted line represents a single bond or a double bond.

The NE≧5-HT SNRI compounds of the invention exclude compounds classified as tricyclic antidepressants, and thus exclude compounds characterized by the above-depicted fused tricyclic nuclei of structures (I), (II), (III), and (IV).

As mentioned above, the NE≧5-HT SNRI compounds useful in the methods and kits of the invention include compounds that inhibit norepinephrine reuptake to a greater extent than serotonin reuptake, as well as compounds that inhibit the reuptake of these two monoamines to an equivalent extent. In one embodiment of the invention, the NE≧5-HT SNRI compounds have a ratio of inhibition of norepinephrine reuptake to serotonin reuptake ("NE:5-HT") in the range of about 1-100:1. In a particular embodiment, the compounds are NE>5-HT SNRI compounds, i.e., compounds that inhibit norepinephrine reuptake to a greater extent than serotonin reuptake. Such NE>5-HT SNRI compounds generally have a NE:5-HT in the range of about 1.1-100:1. That is, such NE>5-HT SNRI compounds are at least about 1.1 to about 100 times more effective at inhibiting norepinephrine reuptake than serotonin reuptake. NE>5-HT SNRI compounds having a NE:5-HT ratio in the range of about 2:1 to about 10:1 may be particularly effective.

Various techniques are known in the art to determine the NE:5-HT of a particular SNRI. In one embodiment, the ratio can be calculated from $IC_{50}$ data for NE and 5-HT reuptake inhibition. For example, it has been reported that for milnacipran the $IC_{50}$ of norepinephrine reuptake is 100 nM, whereas the $IC_{50}$ serotonin reuptake inhibition is 200 nM. See Moret et al., 1985, *Neuropharmacology* 24(12): 1211-1219; Palmier et al., 1989, *Eur J Clin Pharmacol* 37:235-238. Therefore, the NE:5-HT reuptake inhibition ratio for milnacipran based on this data is 2:1. Of course, other IC values such as $IC_{25}$, $IC_{75}$, etc. could be used, so long as the same IC value is being compared for both norepinephrine and serotonin. The concentrations necessary to achieve the desired degree of inhibition (i.e., IC value) can be calculated using known techniques either in vivo or in vitro. See Sanchez et al., 1999, *Cellular and Molecular Neurobiology* 19(4):467-489; Turcotte et al., 2001, *Neuropsychopharmacology* 24(5):511-521; Moret et al., 1985, *Neuropharmacology* 24(12):1211-1219; Moret et al., 1997, *J. Neurochem.* 69(2): 815-822; Bel et al., 1999, *Neuropsychopharmacology* 21 (6):745-754; and Palmier et al., 1989, *Eur J Clin Pharmacol* 37:235-238.

The NE:5-HT of a particular SNRI also can be calculated using equilibrium dissociation constants ($K_D$'s) for norepinephrine and serotonin transporters as described in Tatsumi et al., 1997, *European Journal of Pharmacology* 340:249-258. For example, a NE>5-HT SNRI compound with a $K_D$ of 2 nM for the norepinephrine transporter and a $K_D$ of 8 nM for the serotonin transporter has an NE:5-HT of 4:1.

Yet another means for determining the NE:5-HT of a particular SNRI involves measuring the affinity ($K_i$) of the SNRI for the norepinephrine and serotonin transporters as described in Owens et al., 1997, *JPET* 283:1305-1322. For example, a NE>5-HT SNRI compound with a $K_i$ of 1 nM for the norepinephrine transporter and a $K_i$ of 20 nM for the serotonin transporter has an NE:5-HT of 20:1.

A specific example of a NE≧5-HT SNRI compound that can be used to practice the present invention is milnacipran. Additional NE≧5-HT SNRI compounds that can be used to practice the present invention include, by way of example and not limitation, any of the aminocyclopropane derivatives disclosed in the following references that inhibit norepinephrine reuptake to an equivalent or greater extent than serotonin reuptake (i.e., that have a NE:5-HT ratio that is ≧1:1): WO95/22521; U.S. Pat. No. 5,621,142; Shuto et al., 1995, *J. Med. Chem.* 38:2964-2968; Shuto et al., 1996, *J. Med. Chem.* 39:4844-4852; Shuto et al., 1998, *J. Med. Chem.* 41:3507-3514; Shuto et al., 2001, *Jpn. J. Pharmacol.* 85:207-213; Noguchi et al., 1999, *Synapse* 31:87-96; and U.S. Pat. No. 4,478,836. All of these references are hereby incorporated herein by reference in their entireties.

Aminocyclopropane derivatives can include a compound of the formula I:

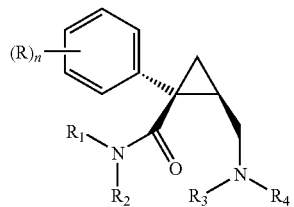

in which: R represents hydrogen, halogen, lower alkyl, lower alkoxy, hydroxy, nitro, or amino; n represents the value 1 or 2; R1 and R2 are independently selected from the group consisting of hydrogen, lower alkyl, lower aryl, and lower-alkylaryl, which aryl or alkylaryl group is optionally substituted by a halogen atom, and, with the adjacent nitrogen atom, a heterocycle of 5 or 6 ring members; R3 and R4 are independently selected from the group consisting of hydrogen, lower alkyl, and, together with the adjacent nitrogen atom, a heterocycle of 5 or 6 ring members optionally containing an additional nitrogen or oxygen heteroatom, or a salt thereof with a therapeutically-acceptable inorganic or organic acid.

In a specific embodiment of the invention, the NE>5-HT SNRI compound is milnacipran. The chemical structure of milnacipran, cis-(±)-2-(aminomethyl)-N,N-diethyl-1-phenyl-yclopropanecarboxamide, is as follows:

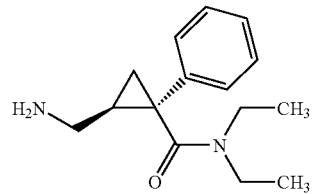

Milnacipran is also known in the art as F2207, TN-912, dalcipran, midalcipran, and midalipran. The NE:5-HT of milnacipran is 2:1. See Moret et al., 1985, *Neuropharmacology* 24(12):1211-1219; Palmier et al., 1989, *Eur J Clin Pharmacol* 37:235-238. Milnacipran and methods for its synthesis are described in U.S. Pat. No. 4,478,836, which is hereby incorporated by reference in its entirety. Additional information regarding milnacipran may be found in the Merck Index, 12th Edition, at entry 6281. Quite significantly, milnacipran has been used as an antidepressant in approximately 400,000 patients, and is known to be non-toxic in humans. In clinical trials at dosages of 100 mg/day or 200 mg/day, milnacipran was well tolerated and usually produced no more adverse effects than placebo (Spencer and Wilde, 1998, *Drugs* 56(3): 405-427).

Those of skill in the art will recognize that NE≧5-HT SNRI compounds such as milnacipran may exhibit the phenomena of tautomerism, conformational isomerism, geometric isomerism and/or optical isomerism. It should be understood that the invention encompasses any tautomeric, conformational isomeric, optical isomeric and/or geometric isomeric forms of the NE≧5-HT SNRI compounds having one or more of the utilities described herein, as well as mixtures of these various different forms. For example, as is clear from the above structural diagram, milnacipran is optically active. It has been reported in the literature that the dextrogyral enantiomer of milnacipran is about twice as active in inhibiting norepinephrine and serotonin reuptake than the racemic mixture, and that the levrogyral enantiomer is much less potent (see, e.g., Spencer and Wilde, 1998, supra; Viazzo et al., 1996, *Tetrahedron Left.* 37(26):4519-4522; Deprez et al., 1998, *Eur. J. Drug Metab. Pharmacokinet.* 23(2):166-171). Accordingly, milnacipran may be administered in enantiomerically pure form (e.g., the pure dextrogyral enantiomer) or as a mixture of dextrogyral and levrogyral enantiomers, such as a racemic mixture. Unless specifically noted otherwise, the term "milancipran" as used herein refers to both enantiomerically pure forms of milnacipran as well as to mixtures of milnacipran enantiomers. Methods for separating and isolating the dextro- and levrogyral enantiomers of milnacipran and other NE≧5-HT SNRI compounds are well-known (see, e.g., Grard et al., 2000, Electrophoresis 2000 21:3028-3034).

It will also be appreciated that in many instances the NE≧5-HT SNRI compounds may metabolize to produce active NE≧5-HT SNRI compounds. The use of active metabolites is also within the scope of the present invention.

It has been reported that milnacipran and its derivatives have antagonistic properties at the NMDA receptor. See Shuto et al., 1995, *J. Med. Chem.* 38:2964-2968; Shuto et al., 1996, *J. Med. Chem.* 39:4844-4852; Shuto et al., 1998, *J. Med. Chem.* 41:3507-3514; and Shuto et al., 2001, *Jpn. J. Pharmacol.* 85:207-213. As a consequence, one particularly useful embodiment of the invention includes NE≧5-HT SNRI compounds that also have NMDA antagonistic properties. The NE≧5-HT SNRI compounds with NMDA receptor antagonistic properties can have $IC_{50}$ values from about 1 nM-100 µM. For example, milnacipran has been reported to have an $IC_{50}$ value of about 6.3 µM. The NMDA receptor antagonistic properties of milnacipran and its derivatives are described in Shuto et al., 1995, *J. Med. Chem.*, 38:2964-2968; Shuto et al., 1996, *J. Med. Chem.* 39:4844-4852; Shuto et al., 1998, *J. Med. Chem.* 41:3507-3514; and Shuto et al., 2001, *Jpn. J. Pharmacol.* 85:207-213. Methods for determining the antagonism and affinity for antagonism are disclosed in Shuto et al., 1995, *J. Med. Chem.* 38:2964-2968; Shuto et al., 1996, *J. Med. Chem.* 39:4844-4852; Shuto et al., 1998, *J. Med. Chem.* 41:3507-3514; Noguchi et al., 1999, *Synapse* 31:87-96; and Shuto et al., 2001, *Jpn. J. Pharmacol.* 85:207-213. Aminocyclopropane derivatives disclosed in WO95/22521; U.S. Pat. No. 5,621,142; Shuto et al., 1995, *J. Med. Chem.* 38:2964-2968; Shuto et al., 1996, *J. Med. Chem.* 39:4844-4852; Shuto et al., 1998, *J. Med. Chem.* 41:3507-3514; Noguchi et al., 1999, *Synapse* 31:87-96; and Shuto et al., 2001, *Jpn. J. Pharmacol.* 85:207-213 that inhibit NE reuptake equal to or greater than 5-HT reuptake and have NMDA antagonistic properties can be used to practice the present invention. These references are hereby incorporated by reference in their entirety.

It has recently been reported that compounds that inhibit reuptake of both NE and 5-HT, such as venlafaxine, duloxetine, milnacipran, and certain TCAs, are effective for the treatment of pain, CFS and FMS, among other maladies, when administered in combination with neurotransmitter precursors such as phenylalanine, tyrosine and/or tryptophan. See WO 01/26623. For example, according to one study reported in WO 01/26623, a patient experiencing, inter alia, fatigue and fibromyalgia, was administered many types of drugs, including many types of non-steroidal anti-inflammatories, both tricyclic and serotonin reuptake inhibiting and noradrenaline reuptake inhibiting antidepressants, and even steroids, without effect. When given a combination of lofepramine (70 mg. bd) and L-phenylalanine (500 mg. bd), the patient experienced a considerable improvement in fatigue and fibromyalgia, which persisted for more than six months. Thus, a compound that inhibits reuptake of both NE and 5-HT was effective only when administered in combination with a neurotransmitter precursor.

Quite surprisingly, the present inventors have discovered that the NE≧5-HT SNRI subclass of SNRI compounds are effective in treating CFS, FMS and pain when administered alone (or in combination with other compounds that are not neurotransmitter precursors such as phenylalanine, tyrosine and/or tryptophan, as will be discussed in more detail, below). Thus, in one embodiment of the invention, the NE≧5-HT SNRI compound is administered alone, or in combination with a compound other than a neurotransmitter precursor such as phenylalanine, tyrosine and/or tryptophan.

The NE≧5-HT SNRI compounds, such as, for example, milnacipran, can be administered adjunctively with other active compounds such as antidepressants, analgesics, muscle relaxants, anorectics, stimulants, antiepileptic drugs, and sedative/hypnotics. Specific examples of compounds that can be adjunctively administered with the NE≧5-HT SNRI compounds include, but are not limited to, gabapentin, pregabalin, pramipexole, I-DOPA, amphetamine, tizanidine, clonidine, tramadol, morphine, tricyclic antidepressants, codeine, cambamazepine, sibutramine, amphetamine, valium, trazodone and combinations thereof. Typically for FMS patients the NE≧5-HT SNRI compounds may be adjunctively administered with antidepressants, anorectics, analgesics, antiepileptic drugs, muscle relaxants, and sedative/hypnotics. For CFS patients, the NE≧5-HT SNRI compounds may be adjunctively administered with antidepressants, anorectics, stimulants, and sedative/hypnotics. For patients suffering from pain the NE≧5-HT SNRI compounds may be adjunctively administered with antidepressants, analgesics, antiepileptic drugs. By adjunctive administration is meant simultaneous administration of the compounds, in the same dosage form, simultaneous administration in separate dosage forms, and separate administration of the compounds. For example, milnacipran can be simultaneously administered with valium, wherein both milnacipran and valium are formulated together in the same tablet. Alternatively, milnacipran could be simultaneously administered with valium, wherein both the milnacipran and valium are present in two separate tablets. In another alternative, milnacipran could be administered first followed by the administration of valium, or vice versa.

The NE≧5-HT SNRI compounds can be administered therapeutically to achieve a therapeutic benefit or prophylactically to achieve a prophylactic benefit. By therapeutic benefit is meant eradication or amelioration of the underlying disorder being treated, e.g., eradication or amelioration of the underlying FMS, CFS or pain disorder, and/or eradication or amelioration of one or more of the physiological symptoms associated with the underlying disorder such that the patient reports an improvement in feeling or condition, notwithstanding that the patient may still be afflicted with the underlying disorder. For example, administration of milnacipran to a patient suffering from FMS provides therapeutic benefit not only when the underlying FMS indication is eradicated or ameliorated, but also when the patient reports decreased fatigue, improvements in sleep patterns, and/or a decrease in the severity or duration of pain.

Although depression is often comorbid in patients suffering from FMS and CFS, and could therefore be characterized as a symptom associated with these disorders, it is well-recognized in the art that NE≧5-HT SNRI compounds such as milnacipran are useful in the treatment of depression.

Accordingly, while successful treatment regimens of the invention contemplate providing an improvement in at least one symptom associated with FMS or CFS, treatment regimens that cause an improvement only in depression are considered ineffective for purposes of the present invention. While improvements in associated psychological symptoms such as depression may be reported, for purposes of the present invention, an improvement in the underlying disorder and/or in at least one of the physiological symptoms associated with the disorder must be reported. Thus, the present invention does not contemplate the treatment of depression alone.

For therapeutic administration, the NE≧5-HT SNRI compound typically will be administered to a patient already diagnosed with the particular indication being treated.

For prophylactic administration, the NE≧5-HT SNRI compound may be administered to a patient at risk of developing FMS, CFS, or pain or to a patient reporting one or more of the physiological symptoms of FMS or CFS, even though a diagnosis of FMS or CFS may not have yet been made. Alternatively, prophylactic administration may be applied to avoid the onset of the physiological symptoms of the underlying disorder, particularly if the symptom manifests cyclically. In this latter embodiment, the therapy is prophylactic with respect to the associated physiological symptoms instead of the underlying indication. For example, the NE≧5-HT SNRI compound could be prophylactically administered prior to bedtime to avoid the sleep disturbances associated with FMS or CFS. Alternatively, the NE≧5-HT SNRI compound could be administered prior to recurrence of pain, or prior to onset of fatigue.

While the invention has been described so far with respect to NE≧5-HT SNRI compounds, the present invention can also be practiced with norepinephrine specific reuptake inhibitors (NARIs). NARIs are a well-recognized class of compounds that specifically inhibit the reuptake of only norepinephrine. An example of a compound that is classified as a NARI is reboxetine.

4.4 Formulation and Routes of Administration

The NE≧5-HT SNRI compounds useful in the present invention, or pharmaceutically acceptable salts thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The term "pharmaceutically acceptable salt" means those salts which retain the biological effectiveness and properties of the compounds used in the present invention, and which are not biologically or otherwise undesirable. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

The compounds, or pharmaceutically acceptable salts thereof, may be administered singly, in combination with other NE≧5-HT SNRI compounds, and/or in cocktails combined with other therapeutic agents. Of course, the choice of therapeutic agents that can be co-administered with the compounds of the invention will depend, in part, on the condition being treated.

The active NE≧5-HT SNRI compounds (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the NE≧5-HT SNRI compounds may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For administration orally, the compounds may be formulated as a sustained release preparation. Numerous techniques for formulating sustained release preparations are described in the following references—U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491. Specifically, sustained release formulations of milnacipran are described in WO 98/08495. These references are hereby incorporated herein by reference in their entireties.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the active compound(s) may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compound(s) may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

4.5 Effective Dosages

Pharmaceutical compositions suitable for use in the present invention include compositions wherein the active ingredient is contained in a therapeutically or prophylactically effective amount, i.e., in an amount effective to achieve therapeutic or prophylactic benefit, as previously discussed. Of course, the actual amount effective for a particular application will depend, inter alia, on the condition being treated and the route of administration. Determination of an effective amount is well within the capabilities of those skilled in the art, especially in light of the disclosure herein.

Therapeutically effective amounts for use in humans can be determined from animal models. For example, a dose for humans can be formulated to achieve circulating concentration that has been found to be effective in animals. Useful animal models of pain are well known in the art. Models of neuropathic pain are described in Zeltser et al., 2000, *Pain* 89:19-24; Bennett et al., 1988, *Pain* 33:87-107; Seltzer et al., 1990, *Pain* 43:205-218; Kim et al., 1992, *Pain* 50:355-363; and Decosterd et al., 2000, *Pain* 87:149-158. An animal model of inflammatory pain using complete Freund's adjuvant is described in Jasmin et al., 1998, *Pain* 75: 367-382. The stress-induced hyperalgesia model described in Quintero et al., 2000, *Pharmacology, Biochemistry and Behavior* 67:449-458 may be used as an animal model of FMS and CFS.

Effective amounts for use in humans can be also be determined from human data for the NE$\geqq$5-HT SNRI compounds used to treat depression. The amount administered can be the same amount administered to treat depression or can be an amount lower than the amount administered to treat depression. For example, the amount of milnacipran administered to treat depression is in the range of about 50 mg-400 mg/day. Thus, either 50 mg-400 mg/day or a lower dose can be administered for practicing the present invention.

Patient doses for oral administration of the NE$\geqq$5-HT SNRI compound typically range from about 1 µg-1 gm/day. For example, for the treatment of FMS, CFS, or pain with milnacipran the dosage range is typically from 25 mg-400 mg/day, more typically from 100 mg-250 mg/day. The dosage may be administered once per day or several or multiple times per day. The amount of the NE$\geqq$5-HT SNRI compound administered to practice methods of the present invention will of course, be dependent on the subject being treated, the severity of the affliction, the manner of administration and the judgment of the prescribing physician. The dose used to practice the invention can produce the desired therapeutic or prophylactic effects, without producing serious side effects.

5. EXAMPLES

5.1 Example 1

Assessment of the Analgesic Properties of Milnacipran in a Rat Pain Model

The rats used in this study are divided into two groups. One group of rats receive a spinal ligation as described in Kim et al., 1992, *Pain* 50(3):355-63 and the other group of rats receive a sham surgery. Each group of rats is further divided into 5 subgroups. Each subgroup receives subcutaneous injection of the vehicle or one of the 4 test doses of milnacipran (5, 10, 25, and 50 mg/kg). The vehicle or milnacipran are administered at a pre-determined time point following the surgeries. Allodynia and thermal hyperalgesia are respectively measured with Von Frey filaments and tail- or paw-flick with a radiant heat source. The allodynia and thermal hyperalgesia measurements are performed at the following time points—prior to surgery, following surgery but prior to the administration of vehicle or milnacipran, and following surgery after the administration of vehicle or milnacipran. The allodynia and thermal hyperalgesia measurements will provide information on the ability of milnacipran to block the development of mechanical allodynia and thermal hyperalgesia.

5.2 Example 2

Assessment of the Efficacy of Milnacipran in an FMS Animal Model

This study is performed on rats or mice that have undergone stress-induced hyperalgesia as described in Quintero et al., 2000, *Pharmacology, Biochemistry and Behavior* 67:449-458. The study consists of 3 groups: placebo, milnacipran subcutaneous pretreatment, and milnacipran treatment. The milnacipran groups are further divided to 4 subgroups and each subgroup is administered 5, 10, 25, or 50 mg/kg of milnacipran. In the milnacipran subcutaneous pretreatment group, the milnacipran is administered prior to the inducement of the stress-induced hyperalgesia. In the milnacipran treatment group, the milnacipran is administered following the inducement of the stress-induced hyperalgesia. Allodynia and thermal hyperalgesia are respectively measured with Von Frey filaments and tail- or paw-flick with a radiant heat source. The allodynia and thermal hyperalgesia measurements are performed at the following time points—prior to both the inducement of stress-induced hyperalgesia and the administration of the milnacipran, prior to the inducement of stress-induced hyperalgesia but following the administration of the milnacipran, following the inducement of stress-induced hyperalgesia but prior to administration of the milnacipran, following both the inducement of stress-induced hyperalgesia and the administration of the milnacipran. The allodynia and thermal hyperalgesia measurements provide information on whether pretreatment or treatment with milnacipran will be effective in the treatment of stress-induced thermal and mechanical hyperalgesia.

5.3 Example 3

Assessment of the Efficacy of Milnacipran in FMS Patients

Approximately 40 subjects are studied for a total of 6 weeks, after being weaned from their previous analgesic or antidepressant medications.

The inclusion criteria for this study is as follows:
1. Patients meet the 1990 American College of Rheumatology criteria for fibromyalgia syndrome.
2. Male or female between the ages of 18 and 70 years. Females are either postmenopausal (no menses for at least 1 year) or status-post oophorectomy (bilateral) or have a negative pregnancy test and be using an accepted method of contraception.
3. Patients have a Gracely intensity pain scale recording (weekly recall) of at least 10 or more on a 20 point scale at baseline.
4. Patients may use non-prescription doses of NSAIDs, aspirin and acetaminophen on a PRN basis for acute pain unrelated to their underlying fibromyalgia.

The patients are divided into 2 groups. The first group is administered 100 mg of milnacipran in a single-dose in the morning, while the second group is administered 50 mg twice a day (i.e., upon awakening and prior to going to sleep). Each patient is then followed for 6 weeks, with visits every two weeks, as follows:

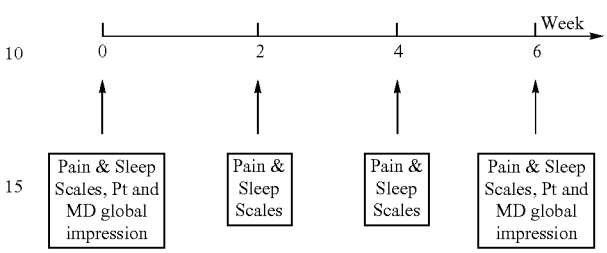

As indicated above, global patient (Pt) and physician (MD) assessments are taken at the beginning and end of the trial. In addition, a total of 4 sets of pain and sleep measures are also performed at 2-week intervals. The pain measure consists of the patient's recall of overall pain over the previous 2-week period as indicated by a 10 cm visual analog scale. The sleep instrument consists of 4 questions taken from the Jenkin's sleep questionnaire. It is expected that milnacipran will produce an improvement in a majority of the patients.

5.4 Example 4

Assessment of the Efficacy of Milnacipran in Patients with Painful Diabetic Neuropathy 20 patients with painful diabetic neuropathy (DN) are studied in a double-blind crossover study. The inclusion criteria for the study are—age of between 18 and 85 years, daily pain of at least "moderate intensity" on the Gracely scale for greater than three months that was present more than 50% of the day, and adequate communication ability demonstrated during a telephone conversation and by completion of a pain diary. Additional inclusion criteria are a diagnosis of diabetes, and distal, symmetrical diabetic neuropathy as assessed by either an unequivocal decrease in pinprick, temperature, or vibration sense in both feet or ankles or decreased or absent ankle jerk reflexes. Exclusion criteria are the presence of another more painful condition, difficulty with ambulation, any unstable disease process, a history of significant substance abuse or alcoholism, liver or kidney disease, or concurrent use of a monoamine oxidase inhibitor.

Milnacipran is compared to placebo in a randomized, double-blind, two-period, crossover study. After discontinuing other medication for pain for two weeks, patients enter a one-week baseline period, followed by two six-week drug treatment periods, separated and concluded by a one-week washout period. The treatments, given in random order, are milnacipran titrated up to maximum-tolerated dose or placebo. A nurse calls the patients every three days to titrate medication dosage and to assess pain, side effects, and study compliance. During the first four weeks of each period (titration phase) the medication is increased by 25 mg/day every three days unless the patient reports complete pain relief, side effects that interfere with daily activities, or unless the maximum dose of 200 mg daily is reached. During weeks 5 and 6 (maintenance phase), the highest well-tolerated dose is maintained at a constant level.

Prior to randomization, a general physical exam and laboratory tests (complete blood count, liver function tests, blood glucose, hemoglobin A1c, blood urea nitrogen, creatinine, electrolytes and urinalysis) is obtained. Diabetics are examined to assure they had adequate blood sugar control before and during the trial. They are instructed to perform daily blood sugar monitoring using a fingerstick and a home glucometer. In addition, a neurologic examination is performed at baseline to identify any area of increased pain to pinprick (hyperalgesia), decreased sensation to pinprick, or pain with stimulation by cotton gauze (allodynia); these studies are conducted every 2 weeks during the trial. In addition, patients record their pain intensity in a diary 3 times daily using the Gracely scale. It is expected that milnacipran will produce an improvement in the majority of patients, as measured by both physician neurological exam and patient diary.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating fibromyalgia, the method consisting essentially of administering to a patient in need thereof
   i) an effective amount of at least one compound selected from milnacipran, a pharmaceutically acceptable salt of milnacipran, or a combination thereof; and
   ii) an effective amount of at least one additional compound selected from pregabalin, a pharmaceutically acceptable salt of pregabalin, or a combination thereof;
   with the proviso that the method excludes administering phenylalanine, tyrosine, or tryptophan.

2. The method of claim 1, wherein the at least one compound selected from milnacipran, a pharmaceutically acceptable salt of milnacipran, or a combination thereof and at least one additional compound are in the same dosage form.

3. The method of claim 1, wherein the at least one compound selected from milnacipran, a pharmaceutically acceptable salt of milnacipran, or a combination thereof and at least one additional compound are in separate dosage forms.

4. The method of claim 3, wherein the at least one compound selected from milnacipran, a pharmaceutically acceptable salt of milnacipran, or a combination thereof and at least one additional compound are administered simultaneously.

5. The method of claim 3, wherein the at least one compound selected from milnacipran, a pharmaceutically acceptable salt of milnacipran, or a combination thereof and at least one additional compound are administered separately.

6. The method of claim 2, wherein the at least one compound selected from milnacipran, a pharmaceutically acceptable salt of milnacipran, or a combination thereof and at least one additional compound are in the same oral dosage form.

7. The method of claim 3, wherein the at least one compound selected from milnacipran, a pharmaceutically acceptable salt of milnacipran, or a combination thereof and at least one additional compound are in separate oral dosage forms.

8. The method of claim 1, wherein the at least one compound selected from milnacipran, a pharmaceutically acceptable salt of milnacipran, or a combination thereof is in tablet form.

* * * * *